United States Patent [19]

Soler

[11] Patent Number: 4,563,467
[45] Date of Patent: Jan. 7, 1986

[54] DERIVATIVES OF N-IMINOPYRIDINIUM BETAINES HAVING ANTI-HYPERTENSIVE AND SALIDIURETIC ACTIVITY AND THEIR PREPARATION

[75] Inventor: José E. Soler, Barcelone, Spain

[73] Assignee: Provesan S.A., Geneva, Switzerland

[21] Appl. No.: 577,273

[22] Filed: Feb. 6, 1984

[30] Foreign Application Priority Data

Feb. 15, 1983 [FR] France .................. 83 02380

[51] Int. Cl.[4] .................. C07D 213/89; C07D 213/56; A61K 31/44
[52] U.S. Cl. .................. 514/336; 514/355; 514/357; 546/283; 546/284; 546/291
[58] Field of Search ............ 546/291, 283, 284; 424/263, 266; 514/336, 355, 357

[56] References Cited

U.S. PATENT DOCUMENTS 4,013,669 3/1977 Parsons .................. 546/291

Primary Examiner—Alan L. Rotman
Attorney, Agent, or Firm—Blakely, Sokoloff, Taylor & Zafman

[57] ABSTRACT

Derivatives of inner salts of aminopyridinium hydroxide and corresponding salts thereof comprising the general formuale I and II

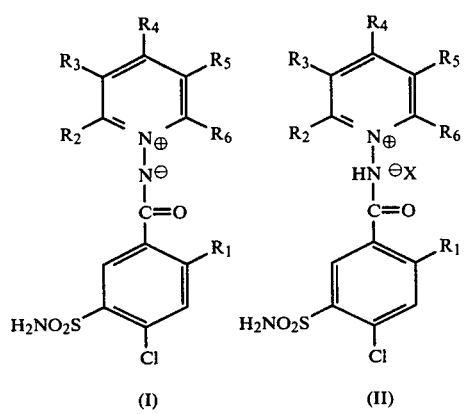

in which:

$R_1$ as selected from the group consisting of a hydrogen and a radical 2-furyl-methyl-amino;

$R_2$, $R_4$ and $R_6$ are all selected from the group consisting of a hydrogen atom, a $C_1$–$C_1$ linear or branched lower alkyl radical and a phenyl radical;

$R_3$ is selected from the group consisting of a hydrogen or a carbamyl radical;

$R_5$ represents a hydrogen; and $X\ominus$ represents a monobasic anion of a pharmaceutically acceptable acid.

5 Claims, No Drawings

DERIVATIVES OF N-IMINOPYRIDINIUM BETAINES HAVING ANTI-HYPERTENSIVE AND SALIDIURETIC ACTIVITY AND THEIR PREPARATION

The present invention relates to novel derivatives of N-iminopyridinium betaines, also referred to as inner salts of aminopyridinium hydroxide, their preparation and their application as medicaments.

The novel derivatives which form the subject of the present invention conform to the general formula I and their corresponding salts conform to the general formula II:

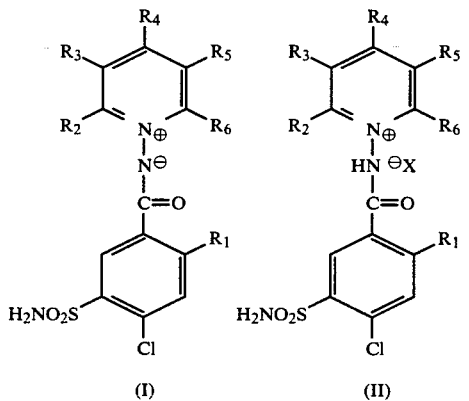

in which:

$R_1$ represents a hydrogen atom, an amino radical or a substituted amino radical such as 2-furyl-methylamino or 2-thenylamino, $R_2$, $R_3$, $R_4$, $R_5$ and $R_6$ are identical or different and represent a hydrogen atom, a $C_1-C_4$ linear or branched lower alkyl radical, an aryl radical, such as phenyl, a carbamyl radical or an amide radical and $X^\ominus$ represents the anion of a pharmaceutically acceptable acid.

Amongst the anions of pharmaceutically acceptable acids there may be mentioned, by way of main examples, those corresponding to the inorganic acids such as chloride, bromide, iodide, nitrate, sulfate and phosphate, or those corresponding to organic acids such as acetate, citrate, oxalate, lactate, tartrate, methanesulfonate, benzenesulfonate, p-toluenesulfonate and cyclohexylsulfamate.

The present invention also relates to the preparation of the derivatives of the general formulae I and II. According to the invention, these derivatives of the general formula I are obtained by employing any of the processes corresponding to reaction schemes A, B and C, and the corresponding salts of the general formula II are obtained by employing the process corresponding to reaction scheme D.

Reaction scheme A

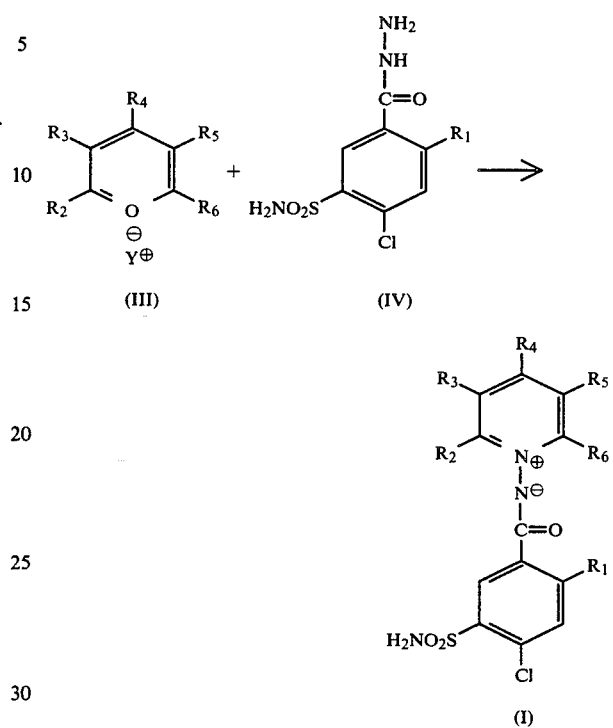

Reaction of a pyrilium salt (III), synthesized by various methods of preparation known per se, and a monosubstituted hydrazine (IV) gives the corresponding salt which, when treated with a base, results in the formation of the betaine of the general formula I.

In the above general formulae III and IV, $R_1$, $R_2$, $R_3$, $R_4$, $R_5$ and $R_6$ have the meanings given earlier and $Y^\ominus$ represents the anions $BF_4^\ominus$, $ClO_4^\ominus$ or $CF_3SO_3^\ominus$.

The pyrilium salts of the formula III can for example be obtained by methods of preparation described in A. T. Balaban & C. D. Nenitzescu, J. Chem. Soc., 1961, 3553–66; P. F. G. Praill & A. L. Whitear, J. Chem. Soc., 1961, 3573–9; A. T. Balaban, Advanc. Heterocycl. Chem., 1969, 10, 241; A. T. Balaban & al, Org. Synt. Coll. Vol. V, 1106–1116; K. Dimroth & al, Org. Synt. Coll. Vol. V, 1135; A. G. Anderson & P. J. Stang, Org. Synt., 1981, 60, 34; E. Elshafie & al., Indian J. Chem. Sect. B, 1981, 20 B(5), 427 and J. A. Van Allan & G. A. Reynolds, J. Org. Chem., 1968, 33, 1102.

The details concerning the implementation of the processes according to reaction scheme A are given by way of illustration in the examples.

Scheme reaction B

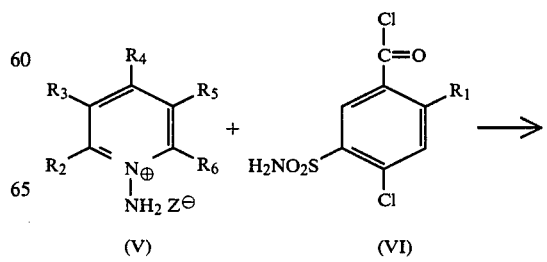

-continued
Scheme reaction B

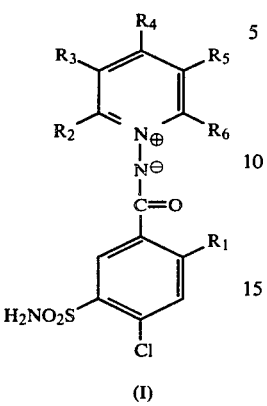

(I)

The N-aminopyridinium salts (V) are obtained by, for example, the method of R. Gosl & A. Meuwsen, Org. Synt., 1963, 43, 1, using aqueous solutions of the corresponding pyridines and of hydroxylamino-O-sulfonic acid, or according to the method of Y. Tamura, J. Minamikawa and M. Ikeda, Synthesis, 1977, 1, by reaction of the corresponding pyridines with the aminating agent, namely O-mesitylenesulfonylhydroxylamine.

Reaction of the N-aminopyridinium salts (V) with an acid chloride (VI) in a basic medium gives the corresponding betaines of the general formula I.

In the general formulae V and VI, $R_1$, $R_2$, $R_3$, $R_4$, $R_5$ and $R_6$ have the meanings indicated above and $Z^\ominus$ represents the anions:

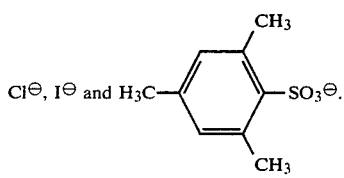

The details relating to the implementation of the processes according to reaction scheme B are given by way of illustration in the examples.

Reaction scheme C

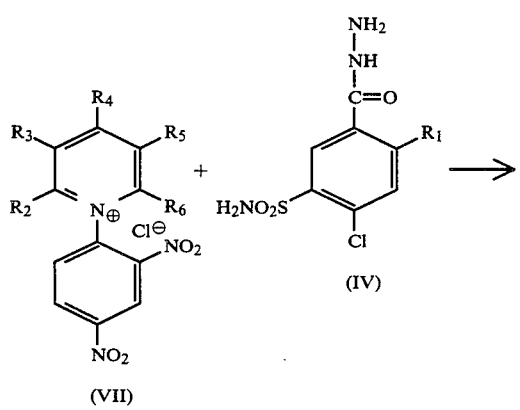

(VII)

-continued
Reaction scheme C

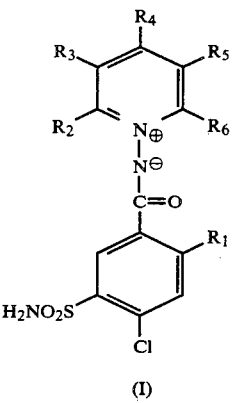

(I)

The N-(2,4-dinitrophenyl)-pyridinium chlorides ("Zincke salts") of the formula (VII) are obtained by, for example, reaction of 1-chloro-2,4-dinitrobenzene with the corresponding pyridine (see T. Zincke, G. Henser and W. Möller, Ann. 1904, 333, 296).

Reaction of the N-(2,4-dinitrophenyl)-pyridinium chloride VII with a monosubstituted hydrazine IV and a tertiary amine as proton acceptor gives the corresponding betaines of the general formula I.

In the above general formulae VII and IV, $R_1$, $R_2$, $R_3$, $R_4$, $R_5$ and $R_6$ have the meanings indicated earlier.

The details relating to the implementation of the processes according to reaction scheme C are given by way of illustration in the examples.

Reaction scheme D

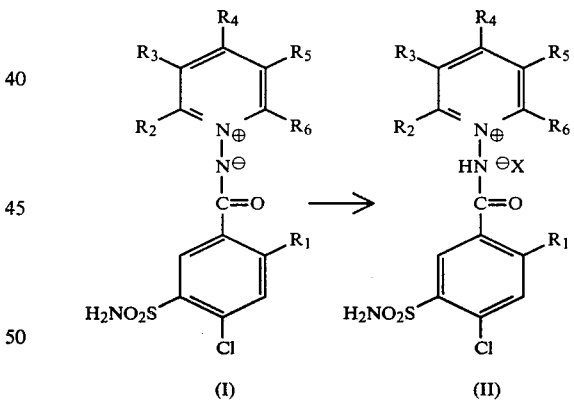

Reaction of the betaine I with an acid $H^\oplus X^\ominus$ in an appropriate solvent such as an alcohol or a ketone gives the corresponding N-aminopyridinium salts of the general formula II.

In the formulae I and II, $R_1$, $R_2$, $R_3$, $R_4$, $R_5$ and $R_6$ and $X^\ominus$ have the meanings indicated earlier.

The details relating to the implementation of the processes according to reaction scheme D are given by way of illustration in the examples.

In view of their good diuretic activity and their very low toxicity, the derivatives of the general formulae I and II are useful as medicaments which can be administered in human or veterinary therapy.

The present invention hence also relates to the application of these derivatives as medicaments as well as to the pharmaceutical compositions which contain these derivatives as the active principle.

The preparation of some derivatives of the general formulae I and II is described below by way of a simple non-limiting example.

EXAMPLE 1

Preparation of 1-[(4-chloro-3-sulfamylbenzoyl)-amino]pyridinium hydroxide inner salt A solution of N-(2,4-dinitrophenyl)-pyridinium chloride (8.4 g, 0.03 mol), 4-chloro-3-sulfamylbenzoylhydrazide (7.5 g, 0.03 mol) and triethylamine (3.2 g, 0.032 mol) in ethanol (250 ml) is refluxed for two hours.

The solution is allowed to cool and is filtered, and the product is washed successively with ethanol, water, ethanol and finally ethyl ether. The precipitate thus obtained is refluxed with 250 ml of dioxane/water (4:1) for 24 hours and the dioxane is then evaporated under reduced pressure. The residue is treated with dilute hydrochloric acid and the mixture is filtered. The aqueous solution is neutralised with sodium hydroxide, stirring being continued for two hours. The mixture is allowed to cool and a precipitate is obtained which is crystallised once from aqueous ethanol, giving 6.2 g (66%) of the inner salt of 1-[(4-chloro-3-sulfamylbenzoyl)-amino]-pyridinium hydroxide, of the formula:

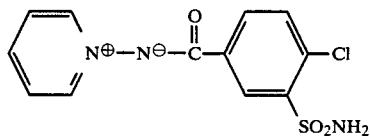

Melting point: 225°–226° C.

Spectroscopic data: IR (KBr): 1625, 1600, 1550, 1355, 1335, 1160 cm$^{-1}$ $^1$H NMR, δ, [DMSO (d$_6$)]: 7.25–8.30 (m, 7H) and 8.60–8.95 (m, 3H).

EXAMPLE 2

Preparation of 1-[(4-chloro-3-sulfamylbenzoyl)-amino]-2,4,6-trimethylpyridinium hydroxide inner salt A solution of freshly prepared trimethylpyrilium tetrafluoborate (3.87 g, 0.0184 mol) and of 4-chloro-3-sulfamylbenzoylhydrazide (5.06 g, 0.0203 mol) in ethanol (60 ml) is refluxed for 4 hours. It is cooled to ambient temperature, with stirring, and 85% strength potassium hydroxide (1.22 g, 0.0185 mol) is added. The mixture is stirred at room temperature for one hour and is then heated to the boil, the potassium tetrafluoborate formed is filtered off hot and the precipitate is washed with ethanol at 60° C. Crystallisation of the concentrated alcoholic solution gives 4.93 g (76%) of 1-[(4-chloro-3-sulfamylbenzoyl)-amino]-2,4,6-trimethylpyridinium hydroxide inner salt of the formula:

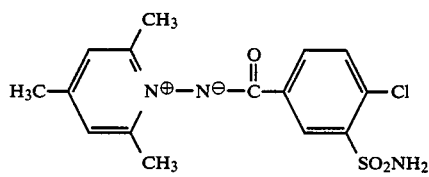

Melting point: 264°–265° C.

Spectroscopic data: IR (KBr): 1640, 1595, 1545, 1360, 1335, 1165 cm$^{-1}$ $^1$H NMR, δ, [DMSO (d$_6$)]: 2.5 (s, 9H), 3.5 (sh, 2H), 7.55 (s, 2H), 7.60 (d, 1H), 8.15 (q, 1H) and 8.65 (d, 1H).

EXAMPLE 3

Preparation of 1-[(4-chloro-3-sulfamylbenzoyl)-amino]-2,6-dimethylpyridinium hydroxide inner salt 1-Amino-2,6-dimethylpyridinium iodide (2.5 g, 0.01 mol) dissolved in water (20 ml) and acetone (10 ml) is treated with potassium carbonate (2.8 g, 0.02 mol). 4-Chloro-3-sulfamylbenzoyl chloride (2.54 g, 0.01 mol) dissolved in acetone (10 ml) is added over 15 minutes. The mixture is stirred for 3 hours at ambient temperature and is then concentrated by evaporating the acetone at a temperature below 40° C. The residue is extracted with chloroform, the extract is dried over Na$_2$SO$_4$ and filtered, and the solvent is evaporated. Recrystallisation of the residue obtained from ethanol gives 2.1 g (62%) of the inert salt of 1-[(4-chloro-3-sulfamylbenzoyl)-amino]-2,6-dimethylpyridinium hydroxide, of the formula:

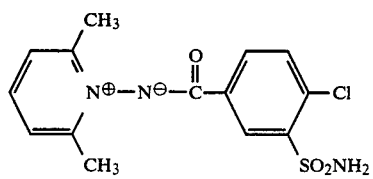

Melting point: 266°–267° C.

Spectroscopic data: IR (KBr): 1632, 1590, 1540, 1360, 1330, 1165 cm$^{-1}$ $^1$H NMR, δ, [DMSO (d$_6$)]: 2.47 (s, 6H) and 7.25–8.50 (m, 8H).

EXAMPLE 4

Preparation of 1-[(4-chloro-3-sulfamylbenzoyl)-amino]-3-carbamylpyridinium hydroxide inner salt A solution of 3-carbamyl-1-(2,4-dinitrophenyl)-pyridinium chloride (6.5 g, 0.02 mol), 4-chloro-3-sulfamylbenzoylhydrazide (5 g, 0.02 mol) and triethylamine (2.15 g, 0.021 mol) in methanol (50 ml) is stirred for 6 hours at ambient temperature. The product is filtered off and washed with methanol, water, methanol and finally ethyl ether. A suspension of the solid obtained in dioxane/H$_2$O (4:1) (100 ml) is refluxed for 15 hours and the dioxane is then evaporated under reduced pressure. The residue is acidified with dilute hydrochloric acid and the product is filtered off and washed with water. The precipitate obtained is stirred with boiling ethanol and the mixture is filtered hot. The precipitate is stirred with a dilute solution of sodium hydroxide for one hour, filtered off and washed with water. 4.1 g (57%) of the inner salt of 1-[(4-chloro-3-sulfamylbenzoyl)-amino]-3-carbamylpyridinium hydroxide of the formula

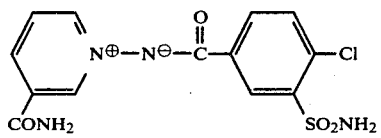

are obtained.

Melting point: 273°–274° C.

Spectroscopic data: IR (KBr): 1700, 1638, 1595, 1545, 1355, 1335, 1175 cm$^{-1}$ $^1$H NMR, δ, [DMSO (d$_6$)]: 7.5–8.75 (m, 9H), 8.9 (d, 1H) and 9.18 (s, 1H).

EXAMPLE 5

Preparation of 1-{[4-chloro-2-(2-furylmethylamino)-5-sulfamylbenzoyl]-amino}-2,4,6-trimethylpyridinium hydroxide inner salt A solution of freshly prepared trimethylpyrilium tetrafluoborate (3.87 g, 0.0184 mol) and of 4-chloro-2-(2-furylmethylamino)-5-sulfamylbenzoylhydrazide (7.21 g, 0.02 mol) in 70 ml of ethanol is refluxed for 6 hours. It is then cooled to ambient temperature with stirring, 85% strength potassium hydroxide (1.22 g, 0.0185 mol) is added and stirring is continued for one hour. The product is filtered off and extracted repeatedly with ethanol. The alcohol solution is concentrated and 4.7 g (55%) of the inert salt of 1-{[4-chloro-2-(2-furylmethylamino)5-sulfamylbenzoyl]-amino}-2,4,6-trimethylpyridinium hydroxide of the formula

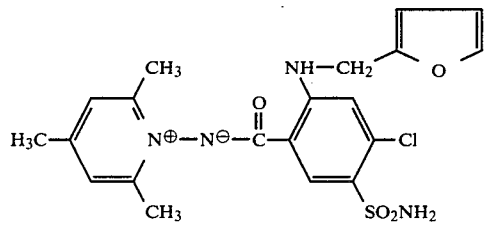

are obtained.

Melting point: 274°–275° C.

Spectroscopic data: IR (KBr): 1638, 1600, 1560, 1355, 1340, 1260, 1165 cm$^{-1}$ $^1$H NMR, δ, [DMSO (d$_6$)]: 2.5 (s, 9H), 4.51 (s, 2H), 6.35 (d, 2H), 6.92 (s, 1H), 7.18 (s, 2H), 7.62 (s, 3H), 8.63 (s, 1H) and 9.5 (sh, 1H).

EXAMPLE 6

Preparation of 1-[(4-chloro-3-sulfamylbenzoyl)-amino]2,4,6-triphenyl-pyridinium hydroxide inner salt A solution of triphenylpyrilium tetrafluoborate (3.96 g, 0.01 mol) and of 4-chloro-3-sulfamylbenzoylhydrazide (2.97 g, 0.011 mol) in ethanol (50 ml) is refluxed for fifteen hours. It is cooled to room temperature, with stirring, and 85% strength potassium hydroxide (0.68 g, 0.0103 mol) is added. Stirring is continued for fifteen minutes and the mixture is then filtered. The filtrate is evaporated to dryness and the residue is recrystallised from benzene, giving 3.0 g (52%) of the inner salt of 1-[(4-chloro-3-sulfamylbenzoyl)-amino]2,4,6-triphenyl-pyridinium hydroxide of the formula

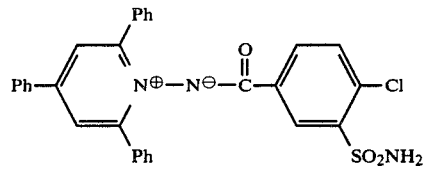

Melting point: 170°–172° C.

Spectroscopic data: IR (KBr): 1628, 1600, 1550, 1350, 1340, 1165 cm$^{-1}$ $^1$H NMR, δ, [DMSO (d$_6$)]: 7.2–7.85 (m, 17H) and 7.94–8.25 (m, 5H).

EXAMPLE 7

Preparation of 1-[(4-chloro-3-sulfamylbenzoyl)-amino]-2,4,6-trimethylpyridinium chloride 10 ml of ethanol saturated with hydrochloric acid are added with stirring to a solution of the inert salt of 1-[(4-chloro-3-sulfamylbenzoyl)-amino]-2,4,6-trimethylpyridinium hydroxide (3.5 g, 0.01 mol) in ethanol (80 ml). After one hour's stirring, the precipitate formed is filtered off and washed with ethanol. 3.6 g (92%) of 1-[(4-chloro-3-sulfamylbenzoyl)-amino]-2,4,6-trimethylpyridinium chloride of the formula

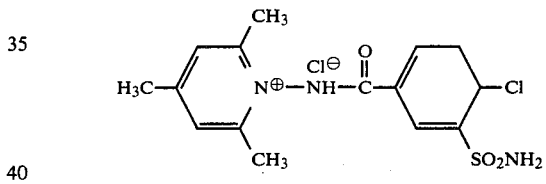

are obtained.

Melting point: 272°–274° C.

Spectroscopic data: IR (KBr): 1705, 1642, 1348, 1165 cm$^{-1}$ $^1$H NMR, δ, [DMSO (d$_6$)]: 2.6 (s, 3H), 2.7 (s, 6H), 4.85 (sh, 2H), 7.7–8.05 (m, 4H) and 8.35–8.65 (m, 2H).

EXAMPLE 8

Preparation of 1-{[4-chloro-2-(2-furylmethylamino)-5-sulfamylbenzoyl]-amino}-2,4,6-trimethylpyridinium chloride hydrochloride 20 ml of ethanol saturated with hydrochloric acid are added, with stirring, to a suspension of the inert salt of 1-{[4-chloro-2-(2-furylmethylamino)-5-sulfamylbenzoyl]-amino}-2,4,6-trimethylpyridinium hydroxide (4.6 g, 0.01 mol) in ethanol (40 ml). After a few seconds, a transparent solution is obtained, which immediately starts to precipitate. The precipitate is filtered off and washed with ethanol, giving 4.9 g (98%) of 1-{[4-chloro-2-(2-furylmethylamino)-5-sulphamylbenzoyl]-amino}-2,4,6-trimethylpyridinium chloride hydrochloride of the formula

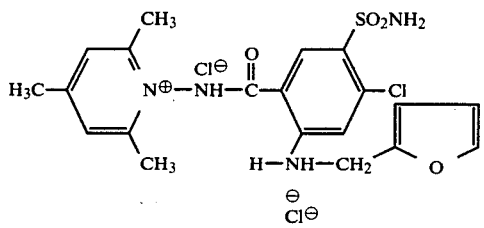

Melting point: 257°-258° C.

Spectroscopic data: IR (KBr): 1668, 1635, 1565, 1355, 1165 cm$^{-1}$ $^1$H NMR, δ, [DMSO (d$_6$)]: 2.6 (s, 3H), 2.7 (s, 6H), 4.6 (s, 2H), 5–6 (sh, 5H), 6.4 (d, 2H), 7.1 (s, 1H), 7.6 (s, 1H), 7.95 (s, 2H) and 8.73 (s, 1H).

EXAMPLE 9

Preparation of 1-[(4-chloro-3-sulfamylbenzoyl)-amino]-2,4,6-triphenyl-pyridinium chloride 10 ml of ethanol saturated with hydrochloric acid are added, with stirring, to a solution of the inert salt of 1-[(4-chloro-3-sulfamylbenzoyl)-amino]-2,4,6-triphenyl-pyridinium hydroxide (5.4 g, 0.01 mol) in ethanol (25 ml). After half an hour's stirring, the precipitate formed is filtered off, giving 5.2 g (90%) of 1-[(4-chloro-3-sulfamylbenzoyl)-amino]-2,4,6-triphenylpyridinium chloride of the formula

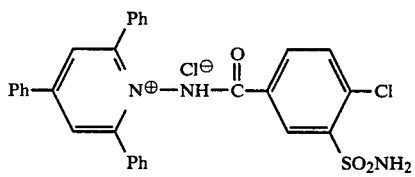

Melting point: 290°-292° C.

Spectroscopic data: IR (KBr): 1700, 1628, 1340, 1170 cm$^{-1}$ $^1$H NMR, , [DMSO (d$_6$)]: 4.5 (sh, 3H), 7.25–7.73 (m, 11H), 7.73–8.3 (m, 7H) and 8.53 (s, 2H).

DIURETIC ACTIVITY

Method of R. M. Taylor and J. G. Topliss, J. Med. Pharm. Chem. 1962, 4, 312

Male Sprague-Dawley (HC/CFY) rats weighting between 150 and 200 grams are used. The animals are kept without food and water for 16 hours before the start of the test. The products are administered as a suspension in a 0.5% strength carboxymethylcellulose suspension in a 0.9% strength sodium chloride solution, using a probang, the amount administered being 50 ml/kg of body weight. The animals are placed in individual metabolism cages and the total amount of urine excreted after the following periods of time is collected: 1, 2, 3, 4, 6 and 8 hours.

The following parameters are determined in the urine: volume (ml/kg); sodium and potassium (milliequivalents/kg/8 h) (flame photometer); chloride (milliequivalents/kg/8 h) (chloride-meter); pH/8 h (pH-meter) and osmotic pressure (osmotic millimols/kg/8 h) (osmometer).

The comparsion animals are given the 0.5% strength carboxymethylcellulose suspension in a 0.9% strength sodium chloride solution in an amount of 50 mg kg of body weight.

Using the Student "t" statistical test for independent values, the values of the abovementioned parameters are compared for the batches treated with a dose of 40 mg/kg and the comparison batch. A product is considered to possess diuretic activity if the difference between the comparison batch and the treated batch is significant (P<0.05) (Blin. C.I., 1970, "Statistics in Biology", Vol. II, McGraw-Hill, New York).

Table 1 below shows the volumes of urine excreted at different intervals of time after administration of 40 mg/kg of various compounds according to the invention.

TABLE 1

| Product | Elimination of urine (ml/kg) | | | | | |
|---|---|---|---|---|---|---|
| | 1 h | 2 h | 3 h | 4 h | 6 h | 8 h |
| Comparison | 4.4 | 12.3 | 17.2 | 21.3 | 25.0 | 27.6 |
| Example 2 | 10.4 *** | 22.3 *** | 30.2 *** | 36.0 *** | 41.5 *** | 45.6 *** |
| Example 1 | 7.3 * | 15.2 N.S | 27.6 *** | 35.4 *** | 40.5 *** | 44.5 *** |
| Example 4 | 5.8 N.S | 8.6 N.S | 19.5 N.S | 24.2 N.S | 31.1 N.S | 37.5 * |
| Example 7 | 6.2 N.S | 18.6 ** | 28.4 *** | 36.1 *** | 47.3 *** | 52.4 *** |
| Example 5 | 1.1 N.S | 3.4 ** | 8.0 * | 12.5 * | 18.4 N.S | 20.7 N.S |
| Example 8 | 0.0 N.S | 11.9 N.S | 19.6 N.S | 28.5 N.S | 34.4 * | 39.2 ** |
| Example 3 | 8.4 N.S | 22.9 ** | 31.9 ** | 36.7 *** | 45.2 *** | 50.7 *** |
| Example 6 | 6.9 N.S | 14.2 N.S | 19.4 N.S | 22.2 N.S | 26.0 N.S | 27.4 N.S |
| Example 9 | 5.2 N.S | 12.6 N.S | 16.8 N.S | 19.0 N.S | 21.5 N.S | 25.3 N.S |
| Chlortalidone | 8.7 *** | 21.0 *** | 30.9 *** | 37.6 *** | 45.6 *** | 49.8 *** |

N.S.: not significant (P > 0.05);
*: significant (P < 0.05);
**: very significant (P < 0.01);
***: highly significant (P < 0.001).

Table 2 below shows the various parameters (Na, K, Cl, pH, osmotic pressure) measured in the total urine excreted over 8 hours, after administration of 40 mg/kg of various compounds according to the invention.

TABLE 2

| Product | Elimination in the urine (over 8 hours) | | | | |
|---|---|---|---|---|---|
| | Na | K | Cl | pH | Osmotic pressure |
| Comparison | 5.6 | 1.2 | 6.4 | 6.1 | 20.7 |
| Example 2 | 9.1 *** | 1.7 *** | 11.8 *** | 6.0 N.S | 29.7 *** |
| Example 1 | 8.3 *** | 1.5 ** | 9.2 *** | 6.6 * | 25.5 *** |
| Example 4 | 6.6 N.S | 1.1 N.S | 7.0 N.S | 6.2 N.S | 20.8 N.S |
| Example 7 | 8 9 *** | 1.6 ** | 9.3 *** | 6.3 N.S | 31.0 *** |
| Example 5 | 3.0 *** | 1.3 N.S | 6.2 N.S | 6.1 N.S | 16.6 N.S |
| Example 8 | 5.9 N.S | 1.2 N.S | 7.2 N.S | 6.7 ** | 23.4 N.S |
| Example 3 | 9.5 *** | 1.8 *** | 11.7 *** | 6.1 N.S | 34.2 *** |
| Example 6 | 6.6 * | 1.1 N.S | 8.1 ** | 6.0 N.S | 25.3 ** |
| Example 9 | 6.0 N.S | 1.2 N.S | 7.5 * | 6.2 N.S | 25.1 ** |
| Chlorthalidone | 9.3 *** | 1.9 *** | 10.8 *** | 6.6 * | 29.9 *** |

By way of a non-limiting example, Table 3 shows the fifty percent effective doses corresponding to the volume of urine and to the osmotic pressure of the compounds of Examples 1, 2 and 3 compared to chlortalidone.

TABLE 3

| Product | $ED_{50}$ (mg/kg)[1] Volume of urine (ml/kg/8 h) | Osmotic pressure (m osmol/kg/8 h) |
|---|---|---|
| Example 1 | 4.1 | 1.9 |
| Example 2 | 4.7 | 1.2 |
| Example 3 | 4.6 | 2.1 |
| Chlortalidone | 6.9 | 7.7 |

[1]The $ED_{50}$ was calculated from the straight line of regression of the plot of the decimal logarithm of the dose against the percentage effect obtained.

ACUTE TOXICITY

The product is administered orally in suspension in 5% strength gum arabic to CFLP-RE albino mice weighing 20–25 g and to CFY-RE Sprague-Dawley rats weighing 125–175 g. The volume administered is 25 ml/kg in the mouse except for the maximum dose of 12,800 mg/kg where a volume of 50 ml/kg is administered, and 10 ml/kg in the rat except for the maximum dose of 12,800 mg/kg where a volume of 30 ml/kg is administered.

It was impossible to determine the 50 percent lethal dose since no deaths occurred.

The results obtained for Example 2 are shown by way of illustration in Table 4.

TABLE 4

| Dose mg/kg | Mortality Mouse ♂ | ♀ | Rat ♂ | ♀ |
|---|---|---|---|---|
| 400 | 0/4 | 0/4 | — | — |
| 800 | 0/4 | 0/4 | — | — |
| 1,600 | 0/4 | 0/4 | 0/4 | 0/4 |
| 3,200 | 0/4 | 0/4 | 0/4 | 0/4 |
| 6,400 | 0/8 | 0/8 | 0/4 | 0/4 |
| 12,800 | 0/8 | 0/8 | 0/8 | 0/8 |

In human therapy, the dose suggested for the derivatives of the present invention is approximately between 20 and 60 mg/day, for example administered in the form of tablets.

A particular galenical form of the derivatives of the present invention is indicated by way of an example.

| Example of the formulation of tablets | |
|---|---|
| 1-[(4-Chloro-3-sulfamylbenzoyl)-amino]-2,4,6-trimethylpyridinium hydroxide inner salt | 0.020 g |
| Lactose | 0.1015 g |
| Starch | 0.027 g |
| Microcrystalline cellulose | 0.018 g |
| Pregelatinised starch | 0.0054 g |
| Polyvinylpyrrolidone | 0.0054 g |
| Magnesium stearate | 0.0018 g |
| Colloidal silicon dioxide | 0.0009 g |
| | 0.1800 g |

The pharmaceutical compositions according to the present invention can, by virtue of their salidiuretic property, be used effectively for the treatment of cardiac, renal and hepatitic edemas, for the treatment of cardiac insufficiency and of arterial hypertension and for blocking lactation.

Of course the pharmaceutical compositions according to the present invention can contain, by way of active principle, one or a plurality of derivatives according to the invention in combination with other active principles possessing different or complementary actions, for example a substance possessing beta-blocking action and useful in the treatment of hypertension.

I claim:

1. Derivatives of inner salts of aminopyridinium hydroxide and corresponding salts thereof comprising the general formulae I and II

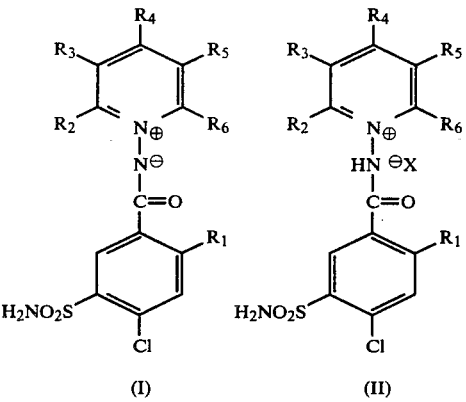

in which:
R₁ as selected from the group consisting of a hydrogen and a radical 2-furyl-methyl-amino;
R₂, R₄ and R₆ are all selected from the group consisting of a hydrogen atom, a C₁—C₁ linear or branched lower alkyl radical and a phenyl radical;
R₃ is selected from the group consisting of a hydrogen or a carbamyl radical;
R₅ represents a hydrogen; and
X⊖ represents a monobasic anion of a pharmaceutically acceptable acid.

2. A derivative of the general formula I as claimed in claim 1 selected from amongst: the inner salt of 1-[(4-chloro-3-sulfamylbenzoyl)amino]-pyridinium hydroxide; the inner salt of 1-[(4-chloro-3sulfamylbenzoyl)-amino]-2,4,6-trimethylpyridinium hydroxide; the inner salt of 1-[(4-chloro-3-sulfamylbenzoyl)amino]-2,6-dimethyl-pyridinium hydroxide; the inner salt of 1-[(4-chloro-3-sulfamylbenzoyl)amino]-3-carbamyl-pyridinium hydroxide; the inner salt of 1-{[(4-chloro-2-(2-furylmethylamino)-5-sulphamylbenzoyl]-amino}-2,4,6-trimethylpyridinium hydroxide; and the inner salt of 1-[(4-chloro-3-sulfamyl-benzoyl)-amino]-2,4,6-trimethylpyridinium hydroxide; and the inner salt of 1-[(4-chloro-3-sulfamylbenzoyl)-amino]-2,4,6-triphenyl-pyridinium hydroxide.

3. A derivative of the general formula II as claimed in claim 1, selected from amongst: 1-[(4-chloro-3-sulfamyl-benzoyl)-amino]-2,4,6-trimethylpyridinium chloride; 1-{[4-chloro-2-(2-furylmethylamino)-5-sulfamylbenzoyl]-amino}-2,4,6-trimethylpyridinium chloride; and 1-[(4-chloro-3-sulfamylbenzoyl)-amino]-2,4,6-triphenyl-pyridinium chloride.

4. An anti-hypertensive composition comprising an effective amount of said derivatives having the general formulae I or II as claimed in claims 1, 2 or 3.

5. A salidiuretic composition, comprising, in addition to a pharmaceutically acceptable carrier, an effective amount of a derivative selected from the group having the general formula I or II according to claims 1, 2, or 3.

* * * * *

UNITED STATES PATENT AND TRADEMARK OFFICE
CERTIFICATE OF CORRECTION

PATENT NO. : 4,563,467
DATED : 1/7/86
INVENTOR(S) : Soler

It is certified that error appears in the above-identified patent and that said Letters Patent is hereby corrected as shown below:

| COLUMN | DESCRIPTION |
|---|---|
| 2 | Reaction Scheme A-(III) delete "$\overset{\ominus}{Y\oplus}$" insert --$\overset{\oplus}{Y\ominus}$-- |
| 2 | Reaction Scheme A-(I) delete "$N_\oplus$" insert --$N_\ominus$-- |
| 2 | Reaction Scheme B-(V) delete "$N_\oplus$" insert --$N_\ominus$-- |
| 3 | Reaction Scheme B-(I) delete "$N_\oplus$" insert --$N_\ominus$-- |

Signed and Sealed this

Ninth Day of August, 1988

*Attest:*

DONALD J. QUIGG

*Attesting Officer*   *Commissioner of Patents and Trademarks*